United States Patent [19]
Wei et al.

[11] Patent Number: 6,063,376
[45] Date of Patent: May 16, 2000

[54] HUMAN DEOXYCYTIDINE KINASE 2

[75] Inventors: Ying-Fei Wei, Darnestown; Ewen F. Kirkness, Olney, both of Md.

[73] Assignee: Human Genome Sciences, Inc., Rockville, Md.

[21] Appl. No.: 08/860,995

[22] PCT Filed: Jan. 13, 1995

[86] PCT No.: PCT/US95/00532

§ 371 Date: Oct. 16, 1997

§ 102(e) Date: Oct. 16, 1997

[87] PCT Pub. No.: WO96/21724

PCT Pub. Date: Jul. 18, 1996

[51] Int. Cl.[7] .............................. A61K 38/45; C12N 9/12
[52] U.S. Cl. .......................................... 424/94.5; 435/194
[58] Field of Search ............................. 435/194; 424/94.5

[56] References Cited

PUBLICATIONS

Bohman et al., Deoxycytidine Kinase from Human Leukemic Spleen: Preparation and Characterization of the Homogeneous enzyme:, Biochemistry, vol. 27, issue 1988, pp. 4258–4265.

Chottiner et al, Cloning and Expression of Human Deoxycytidine Kinase cDNA: Proc. Natl. Acad. Sci. USA, vol. 88, Feb. 1991, pp. 1531–1535.

Song et al, "Genomic Structure and Chromosomal Localization of the Human Deoxycytidine Kinase Gene". Proc. Natl. Acad. Sci. USA, vol. 90, Jan. 1993, pp. 431–434.

Wang et al, "Purification and Characterization of Deoxycytidine Kinase from Acute Myeloid Leukemia Cell Mitochondria", Biochimica et Biophysica Acta, vol. 1202, Feb. 1993, pp. 309–316.

Eriksson et al., "Characterization of Human Deoxycytidine Kinase Correlation with cDNA Sequences", Federation of European Biochemical Societies, vol, 280, No. 2, Mar. 1991, pp. 363–366.

Cheng et al., "Human Deoxycytidine Kinase: Purification and Characterization of the Cytoplasmic and Mitochondrial Isozymes derived from Blast Cells of Acute Myelocytic Leukemia Patients" Biochimica et Biophysica Acta, vol, 481, 1977, pp. 481–492.

Huang et al., "Human Deoxycytidine Kinase Sequence of cDNA Clones and Analysis of Expression in Cell Lines with and without Enzyme Activity", Journal of Biological Chemistry, vol, 264, No. 25, Sep. 1989, pp. 14762–14768.

Johansson et al. Cloning and expression of human deoxyguanosine kinase cDNA. Proc. Nat. Acad. Sci., USA 93: 7258–7262, Jul. 1996.

Kong, X–B et al., Molecular Pharmacology 39: 250–255 (1990).

Antonsson, B. E. et al., Cancer Research 47: 3672–3678 (1987).

Owens, J. K. et al., Cancer Research 52: 2389–2393 (1992).

Datta, N. S. et al., Biochemistry 28: 114–123 (1989).

Creighton, T. E. et al., Evolutionary & Genetic Origins of Protein Sequences :108,109,132,133.

*Primary Examiner*—Robert A. Wax
*Assistant Examiner*—Gabriele E. Bugaisky
*Attorney, Agent, or Firm*—A. Anders Brookes

[57] ABSTRACT

A human deoxycytidine kinase 2 polypeptide and DNA (RNA) encoding such polypeptide and a procedure for producing such polypeptide by recombinant techniques is disclosed. Also disclosed are methods for utilizing such polypeptide for the treatment of malignancies and viral infections. Antagonist against such polypeptides and their use as a therapeutic to treat immunodeficiency disorders are also disclosed. Diagnostic assays for detecting diseases related to mutations in the hdCK2 nucleic acid sequence and the concentration of the polypeptide encoded by such nucleic acid sequence is also disclosed.

16 Claims, 6 Drawing Sheets

```
                                                    -50
                      -70
TCTC GCGGAAGTGATCGCTGTGTGAATCGTGTGGATGGCCGCGGGCGCCTCTTTCT
+-----+-----+-----+-----+-----+-----+
AGAGCCGCCTTCACTAGCGACACACTTAGCACCACCCTACCGGCCGCCCGCGGAGAAAGA
    0                                     10
AAGTCGGCTTCGAGCACCCTTCATTTCCATGGCCAAGAGCCCACTCGAGGGCGTTTCCTC
+-----+-----+-----+-----+-----+-----+
TTCAGCCGAAGCTCGTGGGAAGTAAAGGTACCGGTTCTCGGGTGAGCTCCCGCAAAGGAG
                         M  A  K  S  P  L  E  G  V  S  S
  30                                50                              70
CTCCAGAGGCCTGCACGCGGGGCGCGGGCCCCGAAGGCTCTCCATGAAGGCAACATTGC
+-----+-----+-----+-----+-----+-----+
GAGGTCTCCGGACGTGCGCCCCCGCGCCCGGGGCTTCCGAGAGGTAGCTTCCGTTGTAACG
 S  R  G  L  H  A  G  R  G  P  R  R  L  S  I  E  G  N  I  A
                       110                              130
TGTGGGAAAGTCCACGTTTGTGAAGTTACTCACGAAAACTTACCCAGAATGGCACGTAGC
+-----+-----+-----+-----+-----+-----+
ACACCCTTTCAGGTGCAAACACTTCAATGAGTGCTTTGAATGGTCTTACGTGCATCG
 V  G  K  S  T  F  V  K  L  L  T  K  T  Y  P  E  W  H  V  A
  150                     170                         190
           MATCH WITH FIG. 1B
```

FIG. 1A

MATCH WITH FIG. 1A

TACAGAACCTGTAGCAACATGGCAGAATATCCAGGCTGCTGGCACCCAAAAAGCCTGCAC

ATGTCTTGGACATCGTTGTACCGTCTTATAGGTCCGACGACCGTGGGTTTTTCGGACGTG
T  E  P  V  A  T  W  Q  N  I  Q  A  A  G  T  Q  K  A  C  T
210                          230                         250

TGCCCAAAGTCTTGGAAACTTGCTGGATATGATGTACCGGGAGCCAGCACGATGGTCCTA

ACGGGTTTCAGAACCTTTGAACGACCTATACTACATGGCCCTCGGTGCTGCTACCAGGAT
A  Q  S  L  G  N  L  L  D  M  M  Y  R  E  P  A  R  W  S  Y
270                          290                         310

CACATTCCAGACATTTCCTTTTTGAGCCGCCTGAAAGTACAGCTGGAGCCCTTTCCCTGA

GTGTAAGGTCTGTAAAAGGAAAAAACTCGGGGACTTTCATGTCGACCTCGGGAAGGGACT
T  F  Q  T  F  S  F  L  S  R  L  K  V  Q  L  E  P  F  P  E
330                          350                         370

GAAACTCTTACAGGCCAGGAAGCCAGTACAGATCTTTGAAAGGTCTGTGTACAGTGACAG

CTTTGAGAATGTCCGGTCCTTCGGTCATGTCTAGAAACTTTCCAGACACACATGTCACTGTC
K  L  L  Q  A  R  K  P  V  Q  I  F  E  R  S  V  Y  S  D  R
390                   410                          430

MATCH WITH FIG. 1C

FIG.1B

MATCH WITH FIG. 1B

```
GCTCCACTTTGAGGCTCTGATGAACATTCCAGTGCTGGTGTTGGATGTCAATGATGATTT
 ----+----|----+----|----+----|----+----|----+----|----+----|
CGAGGTGAAACTCCGAGACTACTTGTAAGGTCACGACCACAACCTACAGTTACTACTAAA
 L  H  F  E  A  L  M  N  I  P  V  L  V  L  D  V  N  D  D  F
450                       470                       490

TTCTGAGGAAGTAACCAAACAAGAAGACCTCATGAGAGAGGTAAACACCTTTGTAAAGAA
 ----+----|----+----|----+----|----+----|----+----|----+----|
AAGACTCCTTCATTGGTTGTTCTTCTGGAGTACTCTCTCCATTTGTGGAAACATTTCTT
 S  E  E  V  T  K  Q  E  D  L  M  R  E  V  N  T  F  V  K  N
510                       530                       550

TCTGTAACCAATACCATGATGTTCAGGCTGTGATCTGGGCTCCCTGACTTTCTGAAGCTA
 ----+----|----+----|----+----|----+----|----+----|----+----|
AGACATTGGTTATGGTACTACAAGTCCGACACTAGACCCGAGGGACTGAAAGACTTCGAT
 L  *
570                       590                       610

GAAAAATGTTGTGTCTCCCAACCACCTTTCCATCCCCAGCCCCTCTCATCCCTGGAGCAC
 ----+----|----+----|----+----|----+----|----+----|----+----|
CTTTTTACAACACAGAGGGTTGGTGGAAAGGTAGGGGTCGGGGAGAGTAGGGACCTCGTG
630                       650                       670
```

MATCH WITH FIG. 1D

FIG. 1C

MATCH WITH FIG. 1C

```
TCTGCCGCTCAAGAGCTGGTTTGTTAATTATTGTTAGACTTTGCCATTGTTTCTTTGT
+----+----+----+----+----+----+
AGACGGCGAGTTCTCGACCAAACAATTAATAACAATCTGAAACGGTAACAAAGAAACA
         690                              710                              730

ACCTGAAGCATTTTGAAAATAAAGTTACTTAAGTTATGCTTAAAAAAAAAAAAAAAA
+----+----+----+----+----+----+
TGGACTTCGTAAAACTTTTATTTCAAATGAATTCAATACGAATTTTTTTTTTTTTTT
         750

.
 AAA
+--
 TTT
```

FIG. 1D

```
  1 MATPPKRSCPSFSASSEGTRIKKISIEGNIAAGKSTFVNI  hDCK1
  1 MAKSPLEGVSSSRGLHAGRGPRRLSIEGNIAVGKSTFVKL  hDCK2
  1 MATPPKRFCPSPSTSSEGTRIKKISIEGNIAAGKSTFVNI  mDCK1

41 LKQLCEDWEVVPEPVARWCNVQSTQDEFEELTMSQKNGGN  hDCK1
 41 LTKTYPENHVATEPVATIQNIQAAGT---QKACTAQSLGN  hDCK2
 41 LKQASEDWEVVPEPVARWCNVQSTQEEFEELTSQKSGGN  mDCK1

81 VLQMMYEKPERWSFTFQTYACLSRIRAQLASLNGKLKDAE  hDCK1
 78 LIDMMYREPARWSYTFQTFSFLSRLKVQLEPFPEKLLQAR  hDCK2
 81 VLQMMYEKPERWSFTFQSYACLSRIRAQLASLNGKLKDAE  mDCK1

121 KPVLFFERSVYSDRYIFASNLYESECMNETEWTIYQDWHD  hDCK1
118 KPVQIFERSVYSDR-------------CMNETEWTIYQDWHD  hDCK2
121 KPVLFFERSVYSDRYIFASNLYESDCMNETEWTIYQDWHD  mDCK1

161 WMNNQFGQSLELDGIIYLQATPETCLHRIYLRGNEEQGI  hDCK1
132 WMN---------------------------  hDCK2
161 WMNSQFGQSLELDGIIYLRATPEKCLNRIYLRGRNEEQGI  mDCK1
```

FIG.2A

```
201 P L E Y L E K L H Y K H E S W L L H R T L K T N F D Y L Q E V P I L L D V N E    hDCK1
132 - - - - - - - - L H - - - - - - - - - - - - - - S - E A L M N I P V L V L D V N D    hDCK2
201 P L E Y L E K L H Y K H E S W L L H R T L K T S F D Y L Q E V P V L T L D V N E    mDCK1

241 D F K D - - - K Y E S L V E K V K E F L S T - L    hDCK1
150 D F S E E V T K Q E D L M R E M N T F V K N L      hDCK2
241 D F K D - - - K H E S L V E K V K E F L S T - L    mDCK1
```

Decoration 'Decoration #1': Shade (with solid black) residues that match the Consensus exactly.

FIG. 2B

HUMAN DEOXYCYTIDINE KINASE 2

This application is the U.S. national part, and claims benefit of priority under 35 U.S.C. §371, of copending international patent application Ser. No. PCT/US95/00532, filed Jan. 13, 1995.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is Human Deoxycytidine Kinase 2, sometimes hereinafter referred to as "hdCK2". The invention also relates to inhibiting the action of such polypeptides.

Human deoxycytidine kinase 2 is responsible for the phosphorylation of several deoxyribonucleosides and their analogs. The enzyme has been shown to have broad substrate specificity and plays a physiological role in the maintenance of the normal deoxyribonucleotide pools. Deoxycytidine kinase is also a key enzyme in the phosphorylation of a variety of antineoplastic and antiviral nucleoside analogs including 1-β-D-arabinofuranosylcytosine and dideoxycytidine (Ullman, B. et al, *J.Biol.Chem.*, 263: 12391–12396 (1988)), and deficiency of deoxycytidine kinase actively mediates resistance to these drugs. The enzyme is allosterically regulated by several deoxyribonucleotides and preferentially uses ATP as a phosphate donor for the phosphorylization of deoxycytidine (Ikeda, S. et al., *Bio.Chem.*, 27: 8648–8652 (1988)).

Deoxycytidine kinase isolated from a human lymphoblastic cultured T-cell line had an apparent molecular weight of 60,000 and a Stokes radius of 32 Å. It is thought that the deoxycytidine kinase enzyme is composed of two identical subunits. The rate of deoxycytidine phosphorylation is essentially greatest at pH 7.0 but there is a broad pH optimum ranging from pH 6.5 to pH 9.0. The enzyme also has an absolute requirement for magnesium. In the absence of added divalent cation, deoxycytidine is phosphorylated at about 10% of the rate seen with 2.4 mM magnesium.

An important structural function of the protein is the presence of a probable nucleotide binding domain at amino acids 28–34. The consensus sequence Gly-Xaa-Xaa-Gly-Xaa-Gly-Lys has been reported in several ATP-binding enzymes including a variety of thymidine kinases, the lactobacillus and AMP deaminase and deoxycytidine/deoxyadenosine kinase (Kim, M. et al., *Bio.Chem.Biophys.Res.Commun.*, 156: 92–98 (1988)). The substitution of an alanine residue at position 31, does not prevent effective nucleotide binding. The deoxycytidine kinase protein has a number of substrates including cytosine arabinoside, deoxyguanosine, deoxyadenosine, cytidine, 2-chloro-adenosine and dideoxycytidine. If deoxycytidine kinase is contaminated with uridine-cytidine kinase, cytidine phosphorylation should be inhibited by uridine. While ATP is the preferred phosphate donor, GTP, ITP and XTP had more than 80% of activity as compared to ATP.

Deoxycytidine kinase has been partially purified from many sources (Baxter, A. et al., *Bio.Chem.J.*, 173: 1005–1008 (1978)) including the following human tissues: tonsil lymphocytes, leukemia spleen, T-lymphoblasts, and myeloblasts.

Deoxycytidine kinase is the rate limiting step in the activation of the chemotherapeutic agent cytosine arabinoside to its 5' triphosphate (Mejer, J., *Scand.J.Clin.Lab.Invest.*, 42: 401–406 (1982)). Other clinically important chemotherapeutic agents for which deoxycytidine kinase catalyzes the initial activation of is ara-C, 2-fluoro-9-β-D-arabinofuranosyladenine, and dideoxycytidine (Kufe, D. W. and Spriggs, D. R., *Semin.Oncol.*, 12: 34–48 (1985)).

The polypeptide of the present invention has been putatively identified as human deoxycytidine kinase 2. This identification has been made as a result of amino acid sequence homology to mouse deoxycytidine kinase 1.

In accordance with one aspect of the present invention, there is provided a novel mature polypeptide which is hdCK2, as well as biologically active and diagnostically or therapeutically useful fragments, analogs and derivatives thereof.

In accordance with another aspect of the present invention, there are provided isolated nucleic acid molecules encoding hdCK2, including mRNAs, DNAs, cDNAs, genomic DNAs as well as analogs and biologically active and diagnostically or therapeutically useful fragments thereof.

In accordance with yet a further aspect of the present invention, there is also provided nucleic acid probes comprising nucleic acid molecules of sufficient length to specifically hybridize to hdCK2 sequences.

In accordance with yet a further aspect of the present invention, there is provided a process for producing such polypeptide by recombinant techniques comprising culturing recombinant prokaryotic and/or eukaryotic host cells, containing a hdCK2 nucleic acid sequence, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, to phosphorylate deoxyribonucleosides to ribonucleotides to activate specific anti-cancer and anti-viral drugs, and to preserve the fidelity of the deoxynucleotide pool.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, in the treatment of immunodeficiency diseases.

In accordance with another aspect of the present invention there is provided a method of diagnosing a disease or a susceptibility to a disease, for example, abnormal DNA replication and translation, related to a mutation in hdCK2 nucleic acid sequences and the protein encoded by such nucleic acid sequences.

In accordance with still another aspect of the present invention, there are provided processes for employing the disclosed polynucleotides and polypeptides for research purposes.

These and other aspects of the present invention should be apparent to those skilled in the art from the teachings herein.

The following drawings are illustrative of embodiments of the invention and are not meant to limit the scope of the invention as encompassed by the claims.

FIG. 1A–1D illustrate the cDNA sequence and the corresponding deduced amino acid sequence of hdCK2 polypeptide. The standard 1 letter abbreviations for amino acids is used.

FIG. 2A–2B illustrates the amino acid sequence homology between hdCK1, hdCK2 and mouse dCK1, wherein the shaded areas represent amino acid residues which are the same between the different sequences.

In accordance with an aspect of the present invention, there is provided an isolated nucleic acid (polynucleotide) which encodes for the mature polypeptide having the deduced amino acid sequence of FIG. 1 (SEQ ID No. 2) or for the mature polypeptide encoded by the cDNA of the clone deposited as ATCC Deposit No. 75881 on Aug. 31, 1994. The ATCC (American Type Culture Collection) is located at 10801 University Boulevard, Manassas, Va. 20110-2209, USA.

A polynucleotide encoding a polypeptide of the present invention may be obtained from human ovary, testis, gall bladder, liver, lung, spleen, prostate and heart. The polynucleotide of this invention was discovered in a cDNA library derived from human cycloheximide treated CEM cells. It is structurally related to the deoxycytidine kinase family. It contains an open reading frame encoding a protein of 172 amino acid residues. The protein exhibits the highest degree of homology to human deoxycytidine kinase 1 with 60% identity and 70% similarity over a 90 amino acid stretch. It is also important that the Gly-Xaa-Xaa-Gly-Xaa-Gly-Lys consensus sequence for ATP-binding is conserved.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID No. 1) or that of the deposited clone or may be a different coding sequence which coding sequence, as a result of the redundancy or degeneracy of the genetic code, encodes the same mature polypeptide as the DNA of FIG. 1 (SEQ ID No. 1) or the deposited cDNA.

The polynucleotide which encodes for the mature polypeptide of FIG. 1 (SEQ ID No. 2) or for the mature polypeptide encoded by the deposited cDNA may include: only the coding sequence for the mature polypeptide; the coding sequence for the mature polypeptide and additional coding sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID No. 2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID No. 2) or the same mature polypeptide encoded by the cDNA of the deposited clone as well as variants of such polynucleotides which variants encode for a fragment, derivative or analog of the polypeptide of FIG. 1 (SEQ ID NO. 2) or the polypeptide encoded by the CDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID No. 1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37: 767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 (SEQ ID No. 1) or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a hdCK2 polypeptide which has the deduced amino acid sequence of FIG. 1 (SEQ ID No. 2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID No. 2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID No. 2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the hdCK2 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence (s) (promoter) to direct mRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.$ $coli,$ Streptomyces, $Salmonella$ $typhimurium;$ fungal cells, such as yeast; insect cells such as Drosophila S2 and Spodoptera Sf9; animal cells such as CHO, COS or Bowes melanoma; adenovirus; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, PRIT5 (Pharmacia). Eukaryotic: pWLNEO, pSV2CAT, pOG44, pXT1, pSG (Stratagene) pSVK3, PBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAED-extract mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23: 175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The hdCK2 polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The hdCK2 polypeptides and agonists and antagonists which are polypeptides, discussed below, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Once the hdCK2 polypeptide is being expressed intracellularly via gene therapy, it may be employed to treat malignancies, e.g., tumors, cancer, leukemias and lymphomas and viral infections, since hdCK2 catalyzes the initial phosphorylation step in the formation of cytotoxic triphosphate derivatives of nucleosides such as ara-C, 2-fluoro-9-β-D-arabinofuranosyladenine and dideoxycytidine. These compounds are widely used in the treatment of the above-stated disorders.

hdCK2 may also be employed to maintain normal deoxyribonucleotide pools and therefore ensure correct DNA synthesis.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors and to design diagnostics and therapeutics to treat human disease.

Fragments of the full length hdCK2 gene may be used as a hybridization probe for a cDNA library to isolate the full length hdCK2 gene and to isolate other genes which have a high sequence similarity to the hdCK2 gene or similar biological activity. Probes of this type generally have at least 20 bases. Preferably, however, the probes have at least 30 bases and generally do not exceed 50 bases, although they may have a greater number of bases. The probe may also be used to identify a cDNA clone corresponding to a full length transcript and a genomic clone or clones that contain the complete hdCK2 gene including regulatory and promoter regions, exons, and introns. An example of a screen comprises isolating the coding region of the hdCK2 gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention is also related to the use of the hdCK2 gene as part of a diagnostic assay for detecting diseases or susceptibility to diseases related to the presence of mutated hdCK2, for example, resistance to anti-viral and anti-malignancy compounds.

Individuals carrying mutations in the hdCK2 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324: 163–166 (1986)) prior to analysis. RNA or cDNA may also be used for the same purpose. As an example, PCR primers complementary to the nucleic acid encoding hdCK2 can be used to identify and analyze hdCK2 mutations. For example, deletions and insertions can be detected by a change in size of the amplified product in comparison to the normal genotype. Point mutations can be identified by hybridizing amplified DNA to radiolabeled hdCK2 RNA or alternatively, radiolabeled hdCK2 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230: 1242 (1985)).

Sequence changes at specific locations may also be revealed by nuclease protection assays, such as RNase and S1 protection or the chemical cleavage method (e.g., Cotton et al., PNAS, USA, 85: 4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of hdCK2 protein in various tissues since an over-expression of the proteins compared to normal control tissue samples may detect the presence of a disease or susceptibility to a disease related to malignancy, for example, tumors. Assays used to detect levels of hdCK2 protein in a sample derived from a host are well-known to those of skill in the art and include a radioimmunoassay, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to the hdCK2 antigen, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any hdCK2 proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to hdCK2. Unattached reporter antibody is then washed out. Peroxidase substrates are then added to the dish and the amount of color developed in a given time period is a measurement of the amount of hdCK2 protein present in a given volume of patient sample when compared against a standard curve.

A competition assay may be employed wherein antibodies specific to hdCK2 are attached to a solid support and labeled hdCK2 and a sample derived from the host are passed over the solid support and the amount of label detected, for example by liquid scintillation chromatography, can be correlated to a quantity of hdCK2 in the sample.

A "sandwich" assay is similar to an ELISA assay. In a "sandwich" assay hdCK2 is passed over a solid support and binds to antibody attached to a solid support. A second antibody is then bound to the hdCK2. A third antibody which is labeled and specific to the second antibody is then passed over the solid support and binds to the second antibody and an amount can then be quantitated.

hdCK2 polypeptides may also be employed in a method of screening compounds to identify those which enhance (agonists) or block (antagonists) the phosphorylation activity of hdCK2. An example of such a method comprises isolating hdCK2 from mammalian cells or membrane preparations which express hdCK2, for example HL-60 cells, preparing a reaction mixture, hdCK2 enzyme and the compound to be screened. The reaction mixture is then incubated at elevated temperatures and the deoxycytidine monophosphates formed are detected by the DE-81 disk method (Cheng, Y. C. et al., *Biochem.BioPhys.Acta,* 481: 481–492

(1977)). The hdCK2 activity can be calculated and expressed as fmol of dCMP/min/μg of protein. The ability of the compound to enhance or block the hdCK2 activity as compared to standard activity in the absence of the compound can then be measured.

Human dCK2 is produced and functions intra-cellularly, therefore, any antagonists must be intra-cellular. Potential antagonists to hdCK2 include antibodies which are produced intra-cellularly. For example, an antibody identified as antagonizing hdCK2 may be produced intra-cellularly as a single chain antibody by procedures known in the art, such as transforming the appropriate cells with DNA encoding the single chain antibody to prevent the function of hdCK2.

A potential hdCK2 antagonist also includes an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6: 3073 (1979); Cooney et al, Science, 241: 456 (1988); and Dervan et al., Science, 251: 1360 (1991)), thereby preventing transcription and the production of hdCK2. The antisense RNA oligonucleotide hybridizes to the mRNA in vivo and blocks translation of the mRNA molecule into the hdCK2 polypeptides (antisense—Okano, J. Neurochem., 56: 560 (1991); oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of hdCK2.

Potential hdCK2 antagonists also include a small molecule, which are able to pass through the cell membrane, and bind to and occupy the catalytic site of the polypeptide thereby making the catalytic site inaccessible to substrate such that normal biological activity is prevented. Examples of small molecules include but are not limited to small peptides or peptide-like molecules.

The antagonist may be employed to treat immunodeficiency diseases, since hdCK2 catalyzes a critical step in the synthesis of DATP or dGTP whose accumulation confers cytotoxicity on the T-cell precursors in these disorders. Accordingly, inhibition of the hdCK2 function can eliminate these disorders. The antagonists may be employed in a composition with a pharmaceutically acceptable carrier, e.g., as hereinafter described.

The small molecule agonists and antagonists of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking. into account the routes of administration, symptoms, etc.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256: 495–497), the trioma technique, the human B-cell hybridoma technique (Kozbor et al., 1983, Immunology Today 4: 72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8: 4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52: 456–457 (1973).

EXAMPLE 1

Bacterial Exression and Purification of hdCK2

The DNA sequence encoding hdCK2, ATCC #75881, is initially amplified using PCR oligonucleotide primers corresponding to the 5' and 3' end sequences of the processed hdCK2 gene (minus the signal peptide sequence) and the vector sequences 3' to the hdCK2 gene. Additional nucleotides corresponding to hdCK2 were added to the 5' and 3' sequences respectively. The 5' oligonucleotide primer has the sequence 5' CGGGATCCATGGCCAAGAGCCCACTC 3' (SEQ ID No. 3) contains a BamHI restriction enzyme site followed by 18 nucleotides of hdCK2 coding sequence starting from the presumed terminal amino acid of the processed protein codon. The 3' sequence 5' GCTCTAGAT-TACAGATTCTTTACAAA 3' (SEQ ID No. 4) contains complementary sequences to an XbaI site and is followed by 18 nucleotides at the C-terminus of hdCK2. The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with BamHI and XbaI. The amplified sequences were ligated into pQE-9 and were inserted in frame with the sequence encoding for the histidine tag and the RBS. The ligation mixture was then used to transform *E. coli* strain m15/pREP4 (Qiagen) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 μg/ml) and Kan (25 μg/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 Mm. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized hdCK2 was purified from this solution by chromatography on a Nickel-Chelate column under conditions that allow for tight binding by proteins containing the 6-His tag (Hochuli, E. et al., J. Chromatography 411: 177–184 (1984)). hdCK2 (99% pure) was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmnolar glutathione (oxidized). After incubation in this solution for 12 hours the protein was dialyzed to 10 mmolar sodium phosphate.

EXAMPLE 2

Cloning and expression of hdCK2 using the baculovirus expression system

The DNA sequence encoding the full length hdCK2 protein, ATCC #75881, is amplified using PCR oligonucleotide primers corresponding to the 5' and 3' sequences of the gene:

The 5' primer has-the sequence 5' GCGGGATCCATGG CCAAGAGCCCACTC 3' (SEQ ID No. 5) and contains a BamHI restriction enzyme site (in bold) followed by 18 nucleotides of hdCK2 coding sequence (the initiation codon for translation "ATG" is underlined).

The 3' primer has the sequence 5' GCGGGTACCTT ACAGATTCTTTACAAAGG 3' (SEQ ID No. 6) and contains the cleavage site for the restriction endonuclease Asp718 and 20 nucleotides complementary to the 3' sequence of the hdCK2 gene. The amplified sequences are isolated from a 1% agarose gel using a commercially available kit ("Geneclean," BIO 101 Inc., La Jolla, Calif.). The fragment is then digested with the endonucleases BamHI and Asp718 and then purified again on a 1% agarose gel. This fragment is designated F2.

The vector pA2 (modification of pVL941 vector, discussed below) is used for the expression of the hdCK2 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhidrosis virus (AcMNPV) followed by the recognition sites for the restriction endonucleases BamHI and Asp718. The polyadenylation site of the simian virus (SV)40 is used for efficient polyadenylation. For an easy selection of recombinant viruses the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170: 31–39).

The plasmid is digested with the restriction enzymes BamHI and Asp718 and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. E.coli HB101 cells are then transformed and bacteria identified that contained the plasmid (pBac hdCK2) with the hdCK2 gene using the enzymes BamHI and Asp718. The sequence of the cloned fragment is confirmed by DNA sequencing.

5 μg of the plasmid pBac hdCK2 is co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84: 7413–7417 (1987)).

1 μg of BaculoGold™ virus DNA and 5 μg of the plasmid pBac hdCK2 are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace' medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal", (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus is added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-hdCK2 at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labelled proteins visualized by SDS-PAGE and autoradiography.

EXAMPLE 3

Expression of Recombinant hdCK2 in COS cells

The expression of plasmid, hdCK2 HA is derived from a vector pcDNAI/Amp (Invitrogen) containing: 1) SV40 origin of replication, 2) ampicillin resistance gene, 3) *E.coli* replication origin, 4) CMV promoter followed by a polylinker region, a SV40 intron and polyadenylation site. A DNA fragment encoding the entire hdCK2 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to our target protein allows easy detection of the recombinant protein with an antibody that recognizes the HA epitope.

The plasmid construction strategy is described as follows:

The DNA sequence encoding hdCK2, ATCC #75881, is constructed by PCR using two primers: the 5' primer 5' GCGGGATCCATGGCCAAGAGCCCACTC 3' (SEQ ID No. 7) contains a BamHI site followed by 18 nucleotides of hdCK2 coding sequence starting from the initiation codon; the 3' sequence 5' GCGTCTAGATCAAGCGTAGTCTGG-GACGTCGTATGGGTACAGATT CTTTACAAAGGTG 3' (SEQ ID No. 8) contains complementary sequences to an XbaI site, translation stop codon, HA tag and the last 19 nucleotides of the hdCK2 coding sequence (not including the stop codon). Therefore, the PCR product contains a BamHI site, hdCK2 coding sequence followed by HA tag fused in frame, a translation termination stop codon next to the HA tag, and an XbaI site. The PCR amplified DNA fragment and the vector, pcDNAI/Amp, are digested with BamHI and XbaI restriction enzyme and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant hdCK2, COS cells are transfected with the expression vector by DEAE-DEXTRAN method. (J. Sambrook,. E. Fritsch, T. Maniatis, Molecular Cloning: A Laboratory Manual, Cold Spring Laboratory Press, (1989)). The expression of the hdCK2 HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37: 767 (1984)). Both cell lysate and culture media are precipitated with a HA specific monoclonal antibody. Proteins precipitated are analyzed on 15% SDS-PAGE gels.

EXAMPLE 4

Expression pattern of hdCK2 in human tissue

Northern blot analysis is carried out to examine the levels of expression of hdCK2 in human tissues. Total cellular RNA samples are isolated RNAzol™ B system (Biotecx Laboratories, Inc. Houston, Tex). About 10 μg of total RNA isolated from each human tissue specified is separated on 1% agarose gel and blotted onto a nylon filter. (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column. (5 Prime–3 Prime, Inc. Boulder, Colo.). The filter is then hybridized with radioactive labeled full length hdCK2 gene at 1,000,000 cpm/ml in 0.5M NaPO$_4$, pH 7.4 and 7% SDS overnight at 65° C. After washing twice at room temperature and twice at 60° C. with 0.5×SSC, 0.1% SDS, the filter is then exposed at −70° C. overnight with an intensifying screen.

Numerous modifications and variations of the present invention are possible in light of the above teachings and, therefore, within the scope of the appended claims, the invention may be practiced otherwise than as particularly described.

What is claimed is:

1. An isolated polypeptide comprising a polypeptide selected from the group consisting of:
   (a) a polypeptide consisting of amino acids 1 to 172 of SEQ ID NO:2;
   (b) a polypeptide consisting of amino acids 2 to 172 of SEQ ID NO:2;
   (c) a polypeptide having kinase activity consisting of amino acids 2 to 172 of SEQ ID NO:2, except for at least one conservative amino acid substitution;
   (d) a polypeptide having kinase activity consisting of an amino acid sequence encoded by a polynucleotide which hybridizes to the complement of the coding portion of the polynucleotide of SEQ ID NO:1, wherein said hybridization occurs in 0.5M NaPO$_4$ at pH 7.4 and 7% SDS overnight at 65° C. followed by washing twice at room temperature and twice at 60° C. with 0.5× SSC and 0.1% SDS;
   (e) a fragment of the polypeptide of (a) having kinase activity; and
   (f) a fragment of the polypeptide of (a) which binds to an antibody specific for the polypeptide of (a).

2. The isolated polypeptide of claim 1 wherein said polypeptide is (a).

3. The isolated polypeptide of claim 1 wherein said polypeptide is (b).

4. The isolated polypeptide of claim 1 wherein said polypeptide is (c).

5. The isolated polypeptide of claim 1 wherein said polypeptide is (d).

6. The isolated polypeptide of claim 1 wherein said polypeptide is (e).

7. The isolated polypeptide of claim 1 wherein said polypeptide is (f).

8. An isolated polypeptide comprising a polypeptide selected from the group consisting of:
   (a) the full-length polypeptide encoded by the human cDNA contained in ATCC Deposit No. 75881;
   (b) the full-length polypeptide encoded by the human cDNA contained in ATCC Deposit No. 75881, excepting the N-terminal methionine;
   (c) a polypeptide having kinase activity consisting of the amino acid sequence of the polypeptide of (a), except for at least one conservative amino acid substitution;
   (d) a polypeptide having kinase activity consisting of an amino acid sequence encoded by a polynucleotide which hybridizes to the complement of the coding portion of the human cDNA insert contained in ATCC Deposit No. 75881, wherein said hybridization occurs in 0.5M NaPO$_4$ at pH 7.4 and 7% SDS overnight at 65° C. followed by washing twice at room temperature and twice at 60° C. with 0.5× SSC and 0.1% SDS;
   (e) a fragment of the polypeptide of (a) having kinase activity; and
   (f) a fragment of the polypeptide of (a) which binds to an antibody specific for the polypeptide of (a).

9. The isolated polypeptide of claim 8 wherein said polypeptide is (a).

10. The isolated polypeptide of claim 8 wherein said polypeptide is (b).

11. The isolated polypeptide of claim 8 wherein said polypeptide is (c).

12. The isolated polypeptide of claim 8 wherein said polypeptide is (d).

13. The isolated polypeptide of claim 8 wherein said polypeptide is (e).

14. The isolated polypeptide of claim 8 wherein said polypeptide is (f).

15. A composition comprising the polypeptide of claim 1 in a pharmaceutically acceptable carrier.

16. A composition comprising the polypeptide of claim 8 in a pharmaceutically acceptable.

* * * * *

UNITED STATES PATENT AND TRADEMARK OFFICE
CERTIFICATE OF CORRECTION

PATENT NO.    : 6,063,376
DATED         : May 16, 2000
INVENTOR(S)   : Wei et al.

It is certified that error appears in the above-identified patent and that said Letters Patent is hereby corrected as shown below:

Column 24,
Line 64, claim 16, should read:

16. A composition comprising the polypeptide of claim 8 in a pharmaceutically acceptable carrier.

Signed and Sealed this

Thirteenth Day of May, 2003

JAMES E. ROGAN
*Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 843 BASE PAIRS (B) TYPE: NUCLEIC ACID (C) STRANDEDNESS: SINGLE (D) TOPOLOGY: LINEAR (ii) MOLECULE TYPE: cDNA (xi) SEQUENCE DESCRIPTION: SEQ ID NO:1:

```
TCTCGGCGGA AGTGATCGCT GTGTGAATCG TGGGTGGGAT GGCCGCGGGC GCCTCTTTCT      60

AAGTCGGCTT CGAGCACCCT TCATTTCCAT GGCCAAGAGC CCACTCGAGG GCGTTTCCTC     120

CTCCAGAGGC CTGCACGCGG GGCGCGGGCC CCGAAGGCTC TCCATCGAAG GCAACATTGC     180
```

```
TGTGGGAAAG  TCCACGTTTG  TGAAGTTACT  CACGAAAACT  TACCCAGAAT  GGCACGTAGC       240

TACAGAACCT  GTAGCAACAT  GGCAGAATAT  CCAGGCTGCT  GGCACCCAAA  AAGCCTGCAC       300

TGCCCAAAGT  CTTGGAAACT  TGCTGGATAT  GATGTACCGG  GAGCCAGCAC  GATGGTCCTA       360

CACATTCCAG  ACATTTTCCT  TTTTGAGCCG  CCTGAAAGTA  CAGCTGGAGC  CCTTCCCTGA       420

GAAACTCTTA  CAGGCCAGGA  AGCCAGTACA  GATCTTTGAA  AGGTCTGTGT  ACAGTGACAG       480

GCTCCACTTT  GAGGCTCTGA  TGAACATTCC  AGTGCTGGTG  TTGGATGTCA  ATGATGATTT       540

TTCTGAGGAA  GTAACCAAAC  AAGAAGACCT  CATGAGAGAG  GTAAACACCT  TTGTAAAGAA       600

TCTGTAACCA  ATACCATGAT  GTTCAGGCTG  TGATCTGGGC  TCCCTGACTT  TCTGAAGCTA       660

GAAAATGTT   GTGTCTCCCA  ACCACCTTTC  CATCCCAGC   CCCTCTCATC  CCTGGAGCAC       720

TCTGCCGCTC  AAGAGCTGGT  TTGTTAATTA  TTGTTAGACT  TTGCCATTGT  TTTCTTTTGT       780

ACCTGAAGCA  TTTTGAAAAT  AAAGTTTACT  TAAGTTATGC  TTAAAAAAAA  AAAAAAAAA        840

AAA                                                                          843
```

(2) INFORMATION FOR SEQ ID NO:2:

(i) SEQUENCE CHARACTERISTICS:
        (A) LENGTH: 172 AMINO ACIDS (B) TYPE: AMINO ACID (C) STRANDEDNESS:

(D) TOPOLOGY: LINEAR (ii) MOLECULE TYPE: PROTEIN (xi) SEQUENCE DESCRIPTION: SEQ ID NO:2:

```
Met Ala Lys Ser Pro Leu Glu Gly Val Ser Ser Arg Gly Leu
                 5                  10                  15

His Ala Gly Arg Gly Pro Arg Arg Leu Ser Ile Glu Gly Asn Ile
                20                  25                  30

Ala Val Gly Lys Ser Thr Phe Val Lys Leu Leu Thr Lys Thr Tyr
                35                  40                  45

Pro Glu Trp His Val Ala Thr Glu Pro Val Ala Thr Trp Gln Asn
                50                  55                  60

Ile Gln Ala Ala Gly Thr Gln Lys Ala Cys Thr Ala Gln Ser Leu
                65                  70                  75

Gly Asn Leu Leu Asp Met Met Tyr Arg Glu Pro Ala Arg Trp Ser
                80                  85                  90

Tyr Thr Phe Gln Thr Phe Ser Phe Leu Ser Arg Leu Lys Val Gln
                95                 100                 105

Leu Glu  Pro Phe Pro Glu Lys Leu Leu Gln Ala Arg Lys Pro Val
                110                 115                 120

Gln Ile Phe Glu Arg Ser Val Tyr Ser Asp Arg Leu His Phe Glu
                125                 130                 135

Ala Leu Met Asn Ile Pro Val Leu Val Leu Asp Val Asn Asp Asp
                140                 145                 150

Phe Ser Glu Glu Val Thr Lys Gln Glu Asn Leu Met Arg Glu Val
                155                 160                 165

Asn Thr Phe Val Lys Asn Leu
                170
```

(2) INFORMATION FOR SEQ ID NO:3:

(i) SEQUENCE CHARACTERISTICS:
         (A) LENGTH:  26 BASE PAIRS (B) TYPE:  NUCLEIC ACID (C) STRANDEDNESS:  SINGLE (D) TOPOLOGY:  LINEAR (ii) MOLECULE TYPE:  Oligonucleotide (xi) SEQUENCE DESCRIPTION:  SEQ ID NO:3:

CGGGATCCAT GGCCAAGAGC CCACTC                                              26

(2) INFORMATION FOR SEQ ID NO:4:

(i) SEQUENCE CHARACTERISTICS:
         (A) LENGTH:  26 BASE PAIRS (B) TYPE:  NUCLEIC ACID (C) STRANDEDNESS:  SINGLE (D) TOPOLOGY:  LINEAR (ii) MOLECULE TYPE:  Oligonucleotide (xi) SEQUENCE DESCRIPTION:  SEQ ID NO:4:

GCTCTAGATT ACAGATTCTT TACAAA                                              26

(2) INFORMATION FOR SEQ ID NO:5:

(i) SEQUENCE CHARACTERISTICS:
         (A) LENGTH:  27 BASE PAIRS (B) TYPE:  NUCLEIC ACID (C) STRANDEDNESS:  SINGLE (D) TOPOLOGY:  LINEAR (ii) MOLECULE TYPE:  Oligonucleotide (xi) SEQUENCE DESCRIPTION:  SEQ ID NO:5:

GCGGGATCCA TGGCCAAGAG CCCACTC                                             27

(2) INFORMATION FOR SEQ ID NO:6:

(i) SEQUENCE CHARACTERISTICS:
         (A) LENGTH:  29 BASE PAIRS (B) TYPE:  NUCLEIC ACID (C) STRANDEDNESS:  SINGLE (D) TOPOLOGY:  LINEAR (ii) MOLECULE TYPE:  Oligonucleotide (xi) SEQUENCE DESCRIPTION:  SEQ ID NO:6:

GCGGGTACCT TACAGATTCT TTACAAAGG                                           29

(2) INFORMATION FOR SEQ ID NO:7:

(i) SEQUENCE CHARACTERISTICS:
         (A) LENGTH:  27 BASE PAIRS

```
            (B) TYPE: NUCLEIC ACID (C) STRANDEDNESS: SINGLE (D) TOPOLOGY: LINEAR (ii) MOLECULE TYPE: Oligonucleotide (xi) SEQUENCE DESCRIPTION: SEQ ID NO:7:

GCGGGATCCA TGGCCAAGAG CCCACTC                                                  27

(2) INFORMATION FOR SEQ ID NO:8:

(i) SEQUENCE CHARACTERISTICS:
        (A) LENGTH: 58 BASE PAIRS (B) TYPE: NUCLEIC ACID (C) STRANDEDNESS: SINGLE (D) TOPOLOGY: LINEAR (ii) MOLECULE TYPE: Oligonucleotide (xi) SEQUENCE DESCRIPTION: SEQ ID NO:8:

GCGTCTAGAT CAAGCGTAGT CTGGGACGTC GTATGGGTAC AGATTCTTTA CAAAGGTG       58
```